United States Patent [19]

Reeves

[11] Patent Number: 4,468,619
[45] Date of Patent: Aug. 28, 1984

[54] NON-DESTRUCTIVE DETECTION OF THE SURFACE PROPERTIES OF FERROMAGNETIC MATERIALS

[75] Inventor: Richard Reeves, Lancaster Park, England

[73] Assignee: British Gas Corporation, London, England

[21] Appl. No.: 414,927

[22] Filed: Sep. 3, 1982

Related U.S. Application Data

[63] Continuation of Ser. No. 27,750, Apr. 6, 1979, abandoned, which is a continuation of Ser. No. 870,733, Jan. 19, 1978, abandoned.

[30] Foreign Application Priority Data

Jan. 26, 1977 [GB] United Kingdom ............... 7703189

[51] Int. Cl.$^3$ .................... G01N 27/82; G01R 33/12
[52] U.S. Cl. ...................................... 324/220; 324/235
[58] Field of Search .................. 324/219–221, 324/227, 228, 232, 235, 237, 238, 240, 242, 243, 235

[56] References Cited

U.S. PATENT DOCUMENTS

| | | | |
|---|---|---|---|
| 2,194,229 | 3/1940 | Johnston et al. | 324/221 X |
| 2,892,150 | 6/1959 | Nettles et al. | 324/220 |
| 2,897,438 | 7/1959 | Fearon | 324/221 |
| 3,015,063 | 12/1961 | Ownby | 324/221 |
| 3,114,876 | 12/1963 | Schuster | 324/221 X |
| 3,195,043 | 7/1965 | Gurig et al. | 324/235 |
| 3,284,701 | 11/1966 | Kerbow | 324/221 X |
| 3,317,824 | 5/1967 | Wood | 324/221 |
| 3,356,938 | 12/1967 | Wood | 324/221 |
| 3,359,495 | 12/1967 | McMaster et al. | 324/235 |
| 3,697,867 | 10/1972 | Kleesattel | 324/207 |
| 3,846,697 | 11/1974 | Cila et al. | 324/228 |
| 3,899,734 | 8/1975 | Beaver et al. | 324/220 |
| 4,105,972 | 8/1978 | Smith | 324/220 |
| 4,207,519 | 6/1980 | Zatsepin et al. | 324/235 |

FOREIGN PATENT DOCUMENTS 0171639 11/1965 U.S.S.R. ........................... 324/228

Primary Examiner—Gerard R. Strecker
Attorney, Agent, or Firm—Watson, Cole, Grindle & Watson

[57] ABSTRACT

A method of and apparatus for non-destructive investigation of the surface properties of a body of ferromagnetic material such as a pipeline in which a non-saturating source of magnetic flux is placed adjacent to said surface to create a magnetic circuit having a substantial proportion in non-ferromagnetic material and a sensor is used to measure the magnetic flux in said circuit, an indication of the surface properties of the body being derived from a plurality of such measurements.

7 Claims, 12 Drawing Figures

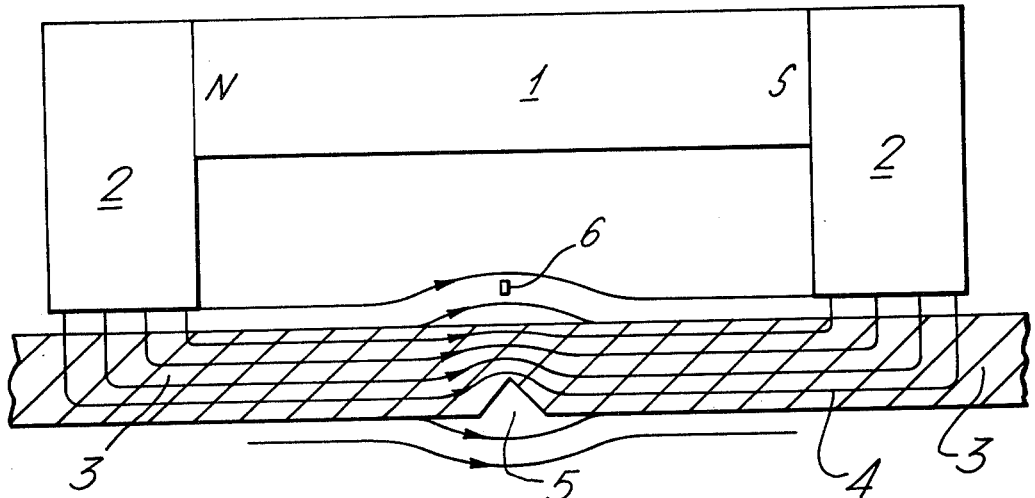
FIG.1.
PRIOR ART
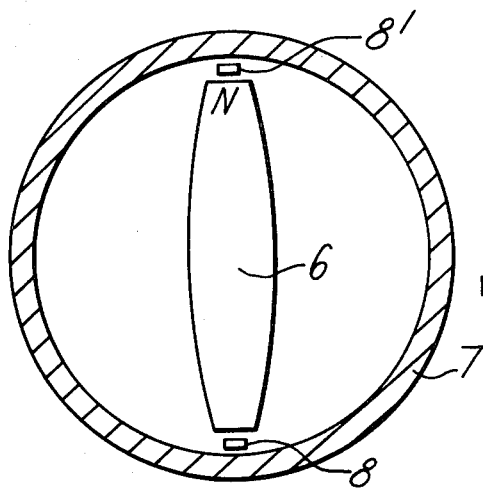
FIG.2.
PRIOR ART
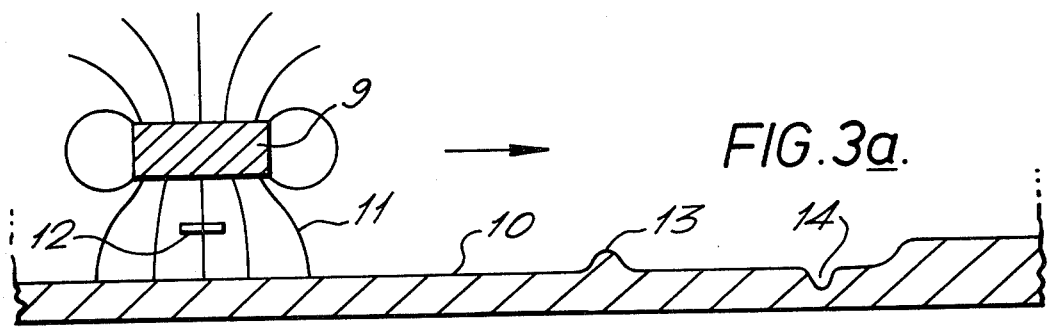
FIG.3a.
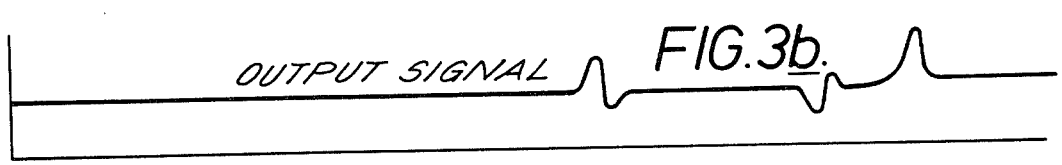
OUTPUT SIGNAL FIG.3b.

NON-DESTRUCTIVE DETECTION OF THE SURFACE PROPERTIES OF FERROMAGNETIC MATERIALS

This is a continuation of application Ser. No. 027,750, filed Apr. 6, 1979, which is a continuation of application Ser. No. 870,733, filed Jan. 19, 1978, and now both abandoned.

BACKGROUND OF THE INVENTION

This invention relates to non-destructive methods of investigating the surface properties of a body of ferromagnetic material and to apparatus therefore. In particular, it is concerned with the determination of the surface profile of the inside of pipelines constructed from materials such as iron or steel.

In the past bodies of ferromagnetic material have been inspected by methods such as the flux leakage method, in which the metal is magnetised in a direction parallel to its surface. At defects, or where regions of the metal body are thinner, some magnetic flux passes into the air and may be detected by sensors, thus giving an indication of the presence of faults.

Another type of magnetic inspection system includes the body to be inspected within a magnetic circuit which incorporates an air gap. Measurement of the field within the gap enables information about the nature of the inspected component to be derived. This system has the advantage that it does not usually require such high intensity magnetic fields as the flux leakage method, but is has the drawback that it is sensitive to variations in, for example, the diameter of the pipeline under test, or other factors affecting the geometry of the magnetic circuit, as well as to surface defects.

Work has been carried out to devise a new improved method of non-destructive testing of bodies of ferromagnetic material.

SUMMARY OF THE INVENTION

Accordingly the present invention provides a non-destructive method of inspecting the internal surface of a pipeline of ferromagnetic material comprising the application of a magnetic field in a direction normal to the internal surface by means of a source of magnetic flux spaced apart therefrom and measuring by means of a magnetic field sensor the component of magnetic field in the vicinity of the internal surface.

According to another aspect, the invention provides apparatus for the non-destructive inspection of the internal surface of a pipeline of ferromagnetic material comprising a source adapted to generate magnetic flux in a direction normal to the internal surface and from a position apart therefrom, and a sensing means to measure the magnetic field in the vicinity of the internal surface.

In a method and apparatus according to the present invention, the magnetic field sensor may be placed between the source and the internal surface.

In a specific embodiment, the invention may incorporate means for measuring the curvature of the internal surface at the position under test.

BRIEF DESCRIPTION OF THE DRAWINGS

The invention will now more particularly be described by way of example with reference to the accompanying drawings in which:

FIG. 1 shows in diagrammatic longitudinal section, known apparatus for detecting surface defects by means of the flux leakage system, FIG. 2 shows in diagrammatic cross-section a known testing system employing magnetic circuits, FIG. 3a is a schematic fragmentary longitudinal section of a pipe illustrating the principle of the method and apparatus in accordance with one aspect of the present invention, FIG. 3b shows the form of the output signal generated by the method and apparatus of FIG. 3a, FIG. 4 shows the profile of the output signals from an array of detectors when scanning a surface defect.

DETAILED DESCRIPTION OF THE PREFERRED EMBODIMENTS

Figure 4:
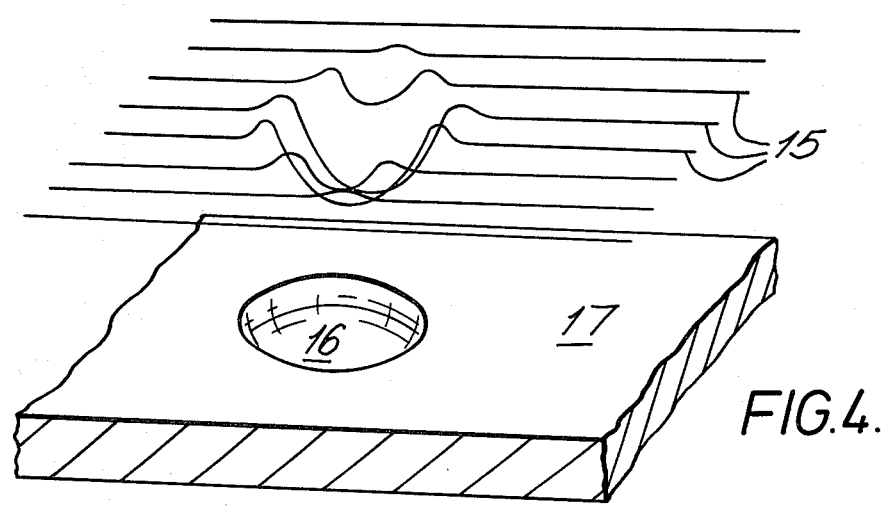

Referring now to the drawings, FIG. 1 shows schematically a known flux leakage system. A powerful magnet 1, having pole pieces 2, induces a relatively strong magnetic field in a region 3 of a pipeline under examination. The lines of force 4 in general are constrained within the ferromagnetic body, but where a fault 5 occurs, there is a higher leakage field, which may be sensed by a detector 6.

Another known system for the non-destructive testing of ferromagnetic bodies is shown in FIG. 2. This is a system for measuring the diameter of ferromagnetic pipelines, and is based on the principle that the reluctance of a magnetic circuit is dependent on the length of air gap in the circuit. In this system, a magnet 6 extends perpendicular to the axis of a cylindrical pipeline 7. Field sensors 8, 8' are mounted in the air gaps between the poles of the magnet and the pipe wall, providiing an indication of the magnetic field strength and hence the diameter of the pipeline.

FIG. 3a illustrates, in schematic form, a surface profile detector in accordance with an aspect of the invention.

Referring to FIG. 3a, a magnet 9, magnetised in a direction normal to the internal surface 10 of a pipeline under test is movable parallel to the surface 10 in the direction of the arrow. Lines of magnetic flux 11 emanate from the magnet and some of these pass into the surface. A sensor 12 senses the magnetic field strength in a position adjacent to the surface. Protuberances 13 and depressions 14 are indicated as increases and decreases in the strength of the component of the field normal to the surface. The output signal derived as the system scans the surface is shown in FIG. 3b.

Figure 5:
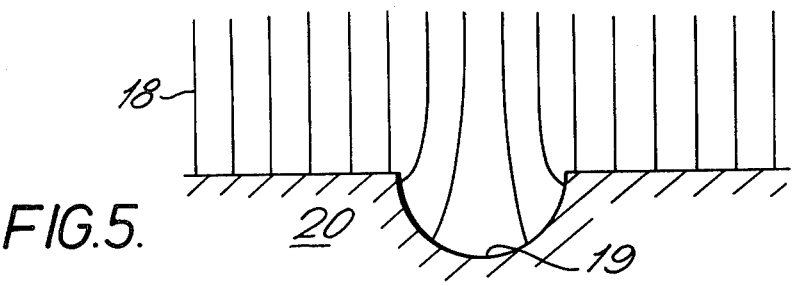
FIG. 5 is a sectional view of a defect in the surface of a body of ferromagnetic material showing the direction taken by the lines of magnetic flux.

It is an important feature of the invention that only the configuration of the internal surface of the pipe adjacent the sensor is significant. Provided the relative permeability of the pipe is high, say greater than 10, and the magnetic flux within the pipe is fairly low, ie substantially below saturation strength, the surface is, to a good approximation, a magnetic equipotential surface. A magnetic equipotential surface is any surface in which the magnetic field lines cross normally, as illustrated in FIG. 5. Under these circumstances, the configuration of the surface of the pipe remote from the sensor and the precise magnetic properties of the pipe under test have a negligible effect on the output signals.

Calculation of the signal to be expected from a given surface profile or the derivation of the profile from records of the sensor signals is a difficult mathematical problem. However, when the normal component is measured, the signal resembles the surface profile in form, although it is smoothed out. FIG. 4 shows the output signals 15 from an array of normal detectors scanning a pit 16 on a metal surface 17.

If the internal pipe surface is substantially flat, the magnetic field may be calculated by the well-known "method of images" in which the fact is utilised that the field in the air space above the plate is the same as that which would arise from the original magnet plus an "image" magnet located on the other side of the plate surface. Using this fact, the distance from magnet to plate surface can be calculated from the sensor signal if the surface is assumed to be flat.

As the magnetic surface is assumed to be equipotential, the lines of flux will enter it normally. FIG. 5 shows the configuration of the lines of flux 18 at a pit 19 in a surface 20. This principle enables fields to be sketched qualitatively.

In general, the higher the sensor is above the surface, the weaker will be the signals from pits and other features. It can be shown that signals from small defects fall off faster with height than signals from large defects and features.

The profile sensors are potentially sensitive to extraneous magnetic material contaminating the surface to be inspected, but in practice the problem is not too severe. Rust is midly magnetic, while mud and dust can contain iron oxides, mill scale and metallic particles from weld spatter. Such materials are found to have very low magnetic permeabilities, often less than 1.1 and usually less than 2.0. If a corrosion pit is filled with such material it is still detectable, but the signal amplitude may be reduced, approximately in accordance with the permeability.

The inner surface of a ferromagnetic pipeline my conveniently be inspected by an inspection vehicle (commonly known as a pig or pigs) carrying a number of magnetic inspection systems in accordance with the invention.

Figure 6A:
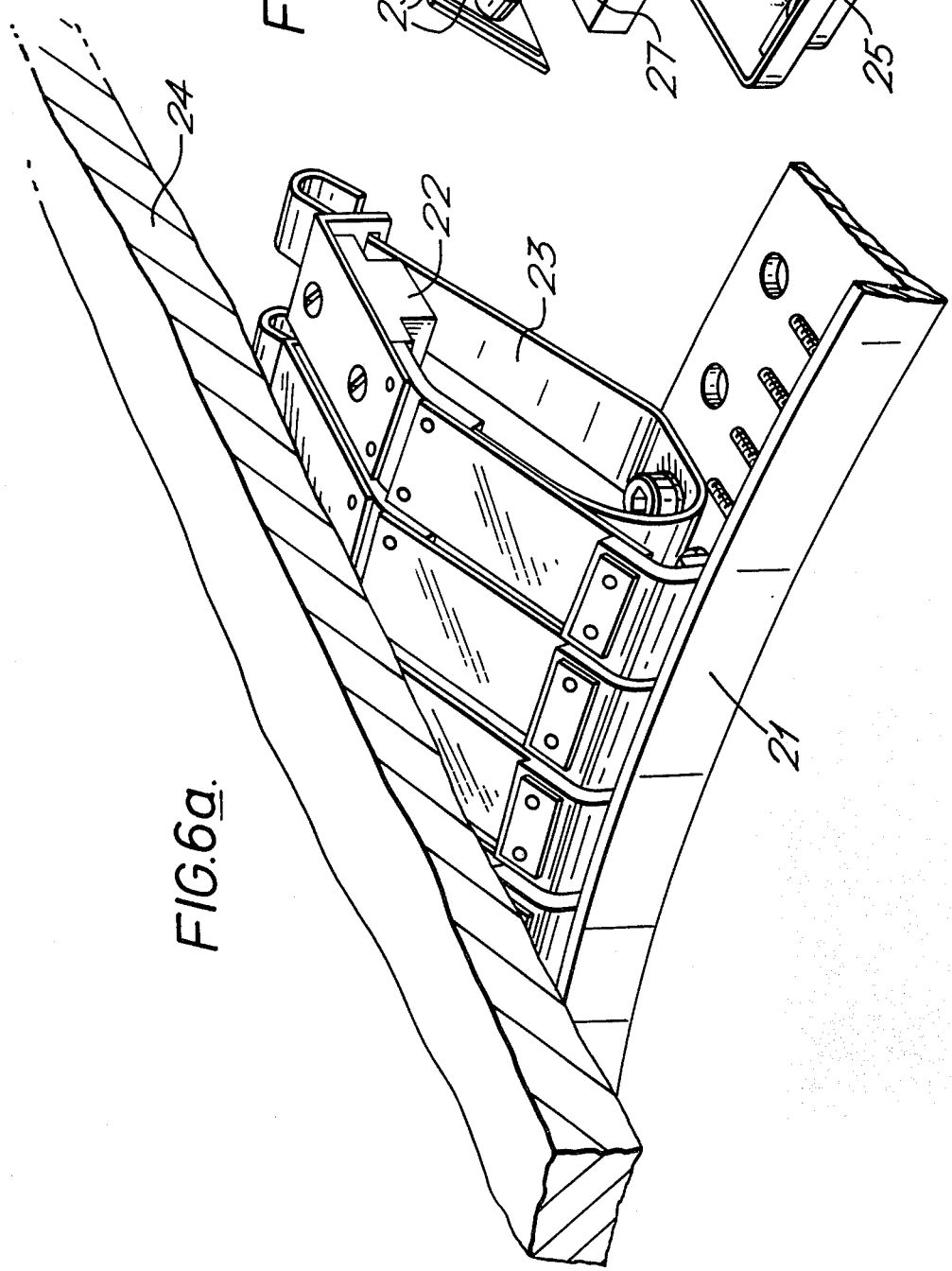
FIGS. 6a and 6b show in perspective projection a practical embodiment of part of the apparatus of FIG. 3a, FIGS. 7 and 8 show alternative embodiments for inspecting a pipeline apparatus.
Figure 6B:
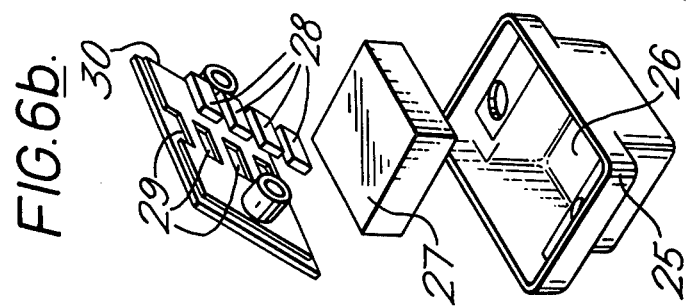

One practical embodiment is shown in FIGS. 6a and 6b. In this arrangement (which is the subject matter of co-pending patent application U.S. Ser. No. 784,911, filed Apr. 5, 1977 and now U.S. Pat. No. 4,105,972) a pig carries a ring 21 on which is mounted a plurality of spring-loaded sledges 23 each carrying a module 22 for measuring magnetic flux. The sledges 23 urge the modules 22 into contact with the inner surface of a pipeline 24. Each module 22 of the measuring system comprises a container 25 having a recess 26 for a magnet 27. An array of sensors 28 is mounted in recesses 29 in the closure member 30.

The sledges 23 are sufficiently close together around the circumference to ensure full inspection coverage. The sledge system accommodates small changes in the pipe diameter and the sledges are arranged to ride easily over welds and other such obstructions. For optimum sensitivity, the sensors are as close to the surface as possible and they are sufficiently close together not to miss a feature of significant size. The magnets are magnetised in the radial direction, ie the direction perpendicular to the pipe surface and are preferably arranged to give a uniform field along the line of sensors.

The sensors may be orientated in two alternative ways. In the first they detect the radial component of the magnetic field, giving an indication of the separation of the sensors and the pipe surface. In this case there will be a signal if the sledge should fail to make good contact with the pipe surface, perhaps because of a layer of sludge lining the pipe surface or perhaps because of malfunction of the sledge mechanism. The second option is for the sensors to detect the axial component of magnetic field parallel to the pipe axis, and therefore there will be no spurious signals caused by lift-off, although defect signals will be reduced in amplitude by the lift-off. With this sensor orientation the relationship between the signals and the surface profile is more complicated.

Figure 7:
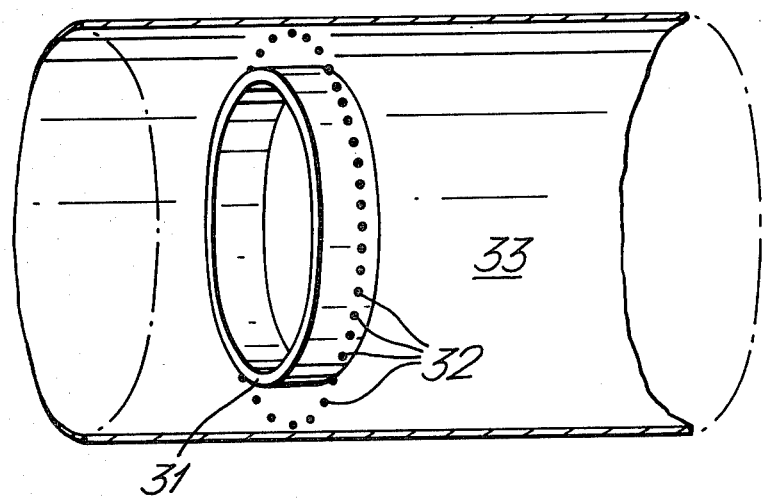

An alternative embodiment is illustrated in FIG. 7 wherein a radially magnetised ring magnet 31, which is fixed relative to a pig body, is used in conjunction with a system of sensors 32 which are urged towards the inner surface of a pipe 33.

Figure 8:
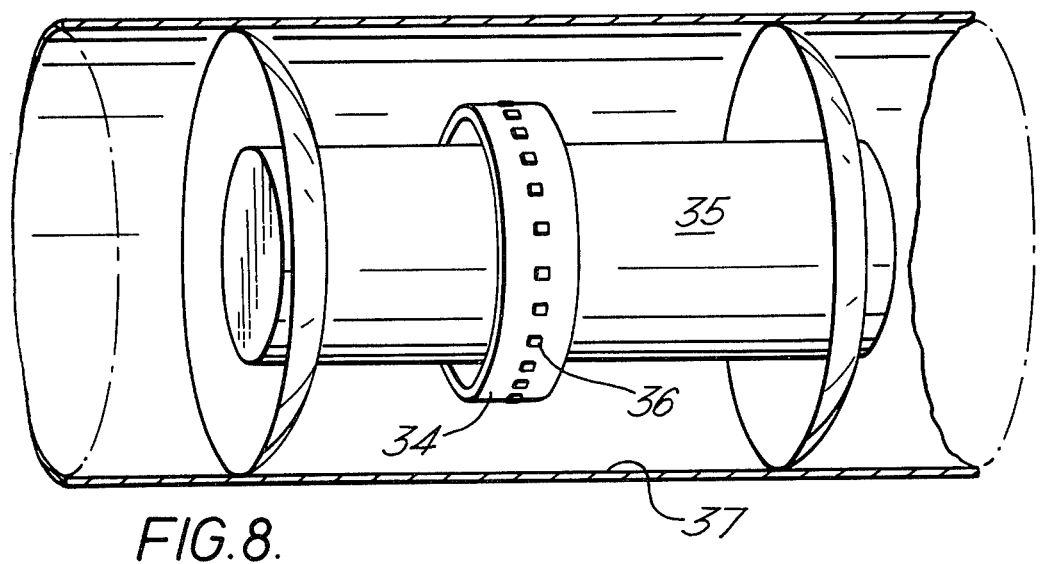

Systems using sledges will not properly inspect a dent, which they will follow, or a corrosion pit so large that the sledge does not bridge over it. In such cases an additional coarse system is useful. One such system shown in FIG. 8 comprises a magnetic ring 34, radially magnetised and mounted on the pig 35, together with a ring of sensors 36 mounted well away from the pipe surface 37. The sensors may be conveniently mounted on the outside of the magnet ring, for example, or even on the inside if a magnet of very low permeability is used. With this arrangement small features give negligible signals but large features show up well.

Additionally, if the radial component of flux normal to the surface is also measured, with a suitable sensor design, then the sensor output is roughly a measure of the distance from the magnet to the pipe surface. The magnet ring then acts as a reference for pipe roundness. The average of the sensor signals gives a measure of the general internal diameter of the pipe.

If the pig's motion should be uneven so that the ring of sensors move relative to the pipe axis, then the uneven motion will be indicated on all the sensor channels. This effect can be removed by suitable electronic processing.

By measuring the pipe curvature as the pig travels along, bends may easily be recognised and any curvature changes, such as might be caused by movement of the pipe due to subsidence or other reasons can be detected.

Figure 9:
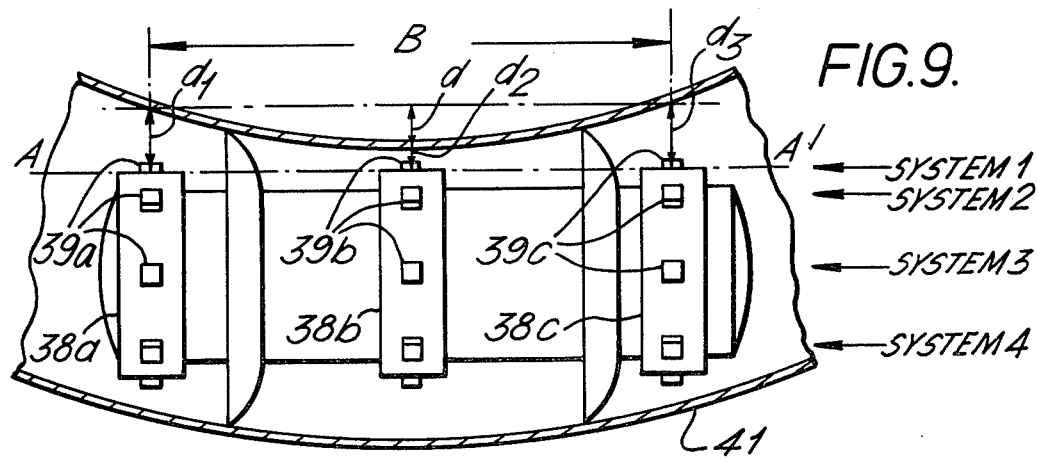
FIG. 9 is a schematic diagram of apparatus for measuring the curvature of the surface of a pipeline of ferromagnetic material.

The arrangement shown in FIG. 9 may be employed for pipe curvature measurement. In this arrangement the pig carries a number of systems spaced around itself each designed to measure the radius of pipe curvature at different orientations. For example, three radially magnetised rings 38a, 38b, 38c are shared by the individual systems, each of which includes a group of three sensors 39a, 39b, 39c spaced apart axially and able to measure the radial component of magnetic field which is representative of the distance from a reference line AA' to the pipe wall 41. If the three groups measure distances $d_1$, $d_2$ and $d_3$, then the distance d can be derived electronically or by off-line analysis by the relationship $$d = d_2 - \tfrac{1}{2}(d_1 + d_3)$$

d together with the base line B enables the pipe curvature to be calculated.

Figure 10:
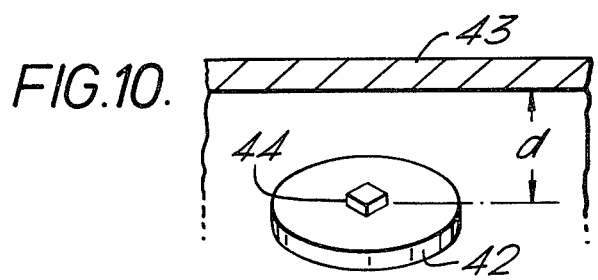
FIG. 10 is a schematic drawing of a displacement sensor for measuring the distance between a reference point and a surface under test.

As an alternative to the rings shown in FIG. 9, individual displacement sensors such as shown in FIG. 10 may be mounted at suitable points. In the latter, magnetic discs 42, magnetised across their thickness, are mounted at a distance d from a pipe wall 43. A normal field sensor 44 is mounted on each side.

It will be appreciated that various modifications may be made without departing from the scope of the invention. The magnet or magnets may be of various shapes or configurations of magnetisation, and any suitable type of magnetic material may be used. Alternatively, the magnetic fields required may be produced by electric currents or may arise from some other nearby magnetic apparatus.

Any suitable type of magnetic field sensor may be used, and either the total magnetic field at a point or over an area may be measured, or a component in a particular direction may be measured. One or many magnets together with one or many sensors may be used. The form of motion of the profile detector is not limited. The magnets may be stationary or moving as may be the component to be measured. Inspection may be quasi-stationary.

Complete coverage of the area to be inspected may be assured by an array of sensors or by sequential motion of one or more sensors to cover the entire area. The magnet may ride well above the area to be inspected with detectors on the surface or both may ride together on the surface, or both may ride together well above the surface.

We claim:

1. A non-destructive method of inspecting the form of the internal surface of a pipeline of ferromagnetic material, comprising: positioning a source of a magnetic field adjacent to, but spaced apart from, said surface to irradiate said internal surface with magnetic flux; maintaining the field emanating from said source at a low magnetic field strength to avoid the generation of leakage flux and such that said internal surface is approximately a magnetic equipotential surface, whereby the lines of flux of the field enter said surface in a direction perpendicular thereto at normal profiles thereof; causing said system to move axially along said pipeline; measuring the component of the magnetic field parallel to the pipeline axis caused by imperfections in the internal pipeline surface at a plurality of locations adjacent the internal pipeline surface during the course of said axial movement with a magnetic field detector located between the magnetic field source and the internal pipeline surface to obtain a corresponding plurality of output measuring signals representative of the profile of the surface of the pipeline in the vicinity of said locations.

2. A method according to claim 1 wherein said magnetic field component parallel to the pipeline axis is measured sequentially at a plurality of axially separated locations using a single sensor.

3. A method according to claim 1 wherein said magnetic field component parallel to the pipeline axis is measured simultaneously at a plurality of circumferentially separated locations using a plurality of sensors.

4. Apparatus for the non-destructive inspection of the form of the internal surface of a pipeline of ferromagnetic material, comprising: means for establishing a magnetic field of low strength to avoid generation of flux leakage and such that the internal surface of the pipeline is approximately a magnetic equipotential surface, whereby the lines of flux of the field enter said surface perpendicular thereto at normal profiles thereof; means for moving said means for establishing a magnetic field axially in relation to said pipeline; location means to position said means for establishing adjacent to, but spaced apart from, said surface; and magnetic field sensor means located between said means for establishing a magnetic field and the internal pipeline surface for the measurement of the component of said magnetic field parallel to the pipeline axis and adjacent to the internal pipeline surface caused by imperfections therein.

5. Apparatus according to claim 4 wherein said magnetic field sensor means includes a plurality of magnetic field sensing means to measure the magnetic field component parallel to the pipeline axis at a plurality of locations adjacent said surface.

6. Apparatus according to claim 4 wherein said means for establishing a magnetic field comprises a ring of magnets radially magnetised.

7. Apparatus according to claim 4 wherein said means for establishing a magnetic field comprises a radially magnetised ring magnet.

* * * * *